United States Patent
Petereit et al.

(10) Patent No.: US 9,700,520 B2
(45) Date of Patent: *Jul. 11, 2017

(54) PH-DEPENDENT CONTROLLED RELEASE PHARMACEUTICAL OPIOID COMPOSITION WITH RESISTANCE AGAINST THE INFLUENCE OF ETHANOL

(75) Inventors: Hans-Ulrich Petereit, Darmstadt (DE); Hema Ravishankar, Chembur (IN); Ashwini Samel, Mumbai (IN)

(73) Assignee: Evonik Roehm GmbH, Darmstadt (DE)

( * ) Notice: Subject to any disclaimer, the term of this patent is extended or adjusted under 35 U.S.C. 154(b) by 1973 days.

This patent is subject to a terminal disclaimer.

(21) Appl. No.: 12/678,406

(22) PCT Filed: Sep. 25, 2007

(86) PCT No.: PCT/EP2007/060131
§ 371 (c)(1),
(2), (4) Date: May 11, 2010

(87) PCT Pub. No.: WO2009/036812
PCT Pub. Date: Mar. 26, 2009

(65) Prior Publication Data
US 2010/0226978 A1  Sep. 9, 2010

(30) Foreign Application Priority Data

Sep. 21, 2007 (IN) .......................... 2130/CHE/2007

(51) Int. Cl.
*A61K 9/50* (2006.01)

(52) U.S. Cl.
CPC ............ *A61K 9/5078* (2013.01); *A61K 9/501* (2013.01); *A61K 9/5026* (2013.01)

(58) Field of Classification Search
None
See application file for complete search history.

(56) References Cited

U.S. PATENT DOCUMENTS

| 6,228,863 | B1 * | 5/2001 | Palermo et al. ............. 514/282 |
| 6,458,389 | B1 | 10/2002 | Debregeas et al. |
| 6,623,758 | B2 | 9/2003 | Rudnic et al. |
| 7,510,729 | B2 * | 3/2009 | Kolter et al. ................. 424/490 |
| 2003/0077297 | A1 * | 4/2003 | Chen et al. ................... 424/400 |
| 2008/0193522 | A1 | 8/2008 | Meier et al. |

FOREIGN PATENT DOCUMENTS

| CN | 1674877 | 9/2005 |
| WO | 03/024430 | 3/2003 |
| WO | 2005/107716 | 11/2005 |
| WO | 2006 125483 | 11/2006 |
| WO | 2007/023325 | 3/2007 |

OTHER PUBLICATIONS

U.S. Appl. No. 13/062,591, filed Mar. 7, 2011, Baer, et al.
U.S. Appl. No. 13/120,112, filed Mar. 21, 2011, Baer, et al.
U.S. Appl. No. 13/256,694, filed Sep. 15, 2011, Baer, et al.
U.S. Appl. No. 13/203,760, filed Aug. 29, 2011, Baer, et al.
U.S. Appl. No. 12/678,429, filed Mar. 16, 2010, Petereit, et al.
Office Action as received in the corresponding Indian patent Application No. 1595/CHENP/2010 dated Dec. 26, 2016.
Office Action dated Jul. 21, 2013, in Israel Patent Application No. 203901 filed Sep. 25, 2007 (English translation only).

* cited by examiner

*Primary Examiner* — Adam C Milligan
*Assistant Examiner* — Sarah Chickos
(74) *Attorney, Agent, or Firm* — Oblon, McClelland, Maier & Neustadt, L.L.P.

(57) ABSTRACT

The invention relates to a pH-dependent controlled release pharmaceutical composition, comprising a core, comprising at least one pharmaceutical active ingredient, which is an opioid, wherein the core is coated at least by one coating layer, controlling the release of the pharmaceutical composition, wherein the coating layer comprises a polymer mixture of i) 40-95% by weight, based on dry weight of the polymer mixture, of at least one water insoluble essentially neutral vinyl polymer, and ii) 5-60% by weight, based on dry weight of the polymer mixture, of at least one anionic polymer or copolymer, which is insoluble in a buffered medium below pH 4.0 and soluble at least in the range from pH 7.0 to pH 8.0, characterized in that the coating layer further contains 110 to 250% by weight, calculated on dry weight of the polymer mixture, of a non-porous inert lubricant and the coating layer is present in an amount of at least 60% by weight calculated on the weight of core.

16 Claims, No Drawings

PH-DEPENDENT CONTROLLED RELEASE PHARMACEUTICAL OPIOID COMPOSITION WITH RESISTANCE AGAINST THE INFLUENCE OF ETHANOL

FIELD OF THE INVENTION

The invention relates to a pH-dependent controlled release pharmaceutical composition for narcotic drugs (opioids) with decreased susceptibility to the influence of ethanol on the release of active compound.

TECHNICAL BACKGROUND

US 2003/0118641 A1 describes a procedure for reducing the abuse potential of oral pharmaceutical forms which contain extractable opioids. In this procedure, resistance to active compound extraction by means of customary domestic solvents, such as isopropyl alcohol, vodka, white wine vinegar, hot water or peroxides, 0.01 HCl in diluted alcohol, should in particular be brought about. It is proposed to formulate the active compound with a matrix-forming polymer and an ion exchange material, e.g. styrene-divinylbenzene polymers, in micronized form. The ion exchange material is crucial for the function of increased resistance to active compound extraction. The matrix-forming polymer obviously serves as a structure-imparting agent for the pharmaceutical core. A long list of possible substances is specified for the matrix-forming polymers, which among many other substances also comprises polymethacrylates. Preferred matrix-forming agents are $C_1$-$C_6$-hydroxyalkylcelluloses.

US 2004/0052731 A1 describes a pharmaceutical form, in particular suitable for opioid active compounds, which should contribute to the reduction of the abuse potential as a result of improper administration. It is proposed to combine a lipophilic active compound variant with a water-insoluble additive, such as, for example, a fatty acid or crosslinked water-soluble polysaccharides.

US 2005/0163856 A1 describes a therapeutic procedure for the treatment of patients suffering from pain with an oxycodone-containing pharmaceutical form having reduced abuse potential as a result of dissolution in a solvent and subsequent improper administration. To this end, the active compound should be formulated with a matrix-forming polymer selected from the group consisting of hydroxypropylcellulose, hydroxypropylmethylcellulose or hydroxyethylcellulose.

WO 2006/002884 A1 describes oral administration forms safeguarded against abuse, which contain a polymer, in particular a polyalkylene oxide, having a fracture resistance of at least 500 N.

WO 2006/094083 A1 describes a pharmaceutical form having controlled venlafaxine release characteristics. For the reduction of the abuse potential by addition of ethanol, the active compound is integrated into a matrix of a gelling, crosslinked polymer, e.g. xanthan. Further hydrophobic polymers, inter alia also polymethacrylates, can be added as additives.

WO 2006/125483 describes the use of a polymer mixture for the production of coated pharmaceutical formulations and pharmaceutical formulations with mixed polymer coatings. The polymer mixtures are intended to provide modified release profiles, tailor made for the certain therapeutically requirements of different pharmaceutical ingredients, which cannot be achieved by using standard polymers. There is no indication about ethanol resistant pharmaceutical forms. In the examples pharmaceutical forms coated with mixtures of Eudragit® NE and Eudragit® FS at ratios from 5 to 50% by weight of Eudragit® FS are described. However no talcum is used in the examples or recommended in the description at high amounts as used in the present invention. The suitable thickness of the coatings from 2-20% by weight, based on the weight of the core, is much lower than those thicknesses required for the present invention.

WO 1994/0022431 A1 describes an oral pharmaceutical preparation containing a therapeutically effective amount of morphine for administration. It consists of at least 50 individual particles with an individual particle size in the range of 0.7 to 1.4 mm. Each particle has a core containing a salt of morphine coated with a barrier layer. The barrier layer contains at least one water insoluble component selected from the group of ethyl cellulose, copolymers synthesized from acrylic or methacrylic esters and natural waxes, and a plastisizer, for providing drug release through the coating barrier layer which is substantially independent of pH in the range of 1.0 to 7.0. The resulting serum concentration of morphine obtained is at least 50% of the maximum serum concentration during at least 12 hours after the administration of a single dose of said preparation.

US 2007/053698 discloses methods of sustained release administration of opioids, including but not limited to hydromorphone and oxycodone, that exhibit improved properties with respect to co-ingestion with aqueous alcohol.

DEFINITIONS

A pH-Dependent Controlled Release Pharmaceutical Composition

A pH-dependent controlled release pharmaceutical composition means a pharmaceutical composition including a pharmaceutical ingredient, which is an opioid, and which is formulated with pharmaceutically acceptable film forming polymers and optionally with other pharmaceutically acceptable excipients, where the pharmaceutical composition shows a pH-dependent controlled release of the pharmaceutical ingredient.

pH-Dependent Controlled Release pH-dependent controlled release of the pharmaceutical ingredient means that when the pharmaceutical composition is exposed in an in-vitro dissolution test to buffered USP media with different pH values of about 1 pH step in the range from about pH 1 to about pH 7, the amount of pharmaceutical ingredient which is released or dissolved in the medium at a certain time interval differs significantly in the media with different pH values.

Buffered USP media with different pH values are known to the person skilled in the art. USP media with different pH values may have pH values for instance of pH 1.2, pH 2.0, pH 5.8, pH 6.8 and pH 7.4. An in-vitro dissolution test may be carried out in an USP dissolution apparatus, for instance apparatus No. II (paddle), 37° C., dissolution agitation 50 rpm, A certain time interval may be for instance 1, 2, 3, 4, 5, 6, 7, 8, 9 or 10 hours or even more hours.

The dissolution rate in the media with different pH values differs significantly when tested in media with different pH values pH 1.2, 2.0, 4.5, 6.8 and 7.4.

For illustration, in contrast to the pH-dependent controlled release behaviour of the present invention a typically pH independent controlled release behaviour is shown for instance in WO1994/022431A1 (s. especially p. 13, table 5).

Especially the pH release behaviour of the pharmaceutical composition of the present invention is pH dependent because of its gastric resistance, which means that in an USP medium of pH 1.2 there is not more than 10% of the pharmaceutical ingredient released within 2 hours, while at higher pH values, for instance at pH 7.4, there is significantly more than 10% of the pharmaceutical ingredient released within 2 hours. In contrast the pH independent controlled release form of WO1994/022431A1 (s. p. 13, table 5) may show an identical release rate of 15% after 2 hours in a pH 1.2 or pH 7.4 buffered medium.

Opioids

An opioid in the sense of the present invention means an agent that binds to an opioid receptor as found in the central nervous system or in the gastrointestinal tract of man or mammalian animals and shows a more or less strong narcotic effect (opioid agonist). In contrast to opioids, opioid antagonists, like for instance naloxone, can also bind to opioid receptors, but do not show strong narcotic effects. An opioid in the sense of the present invention comprise opioids selected from opium alkaloids, semi-synthetic opioids or wholly synthetic opioids.

Opioids in the sense of the present invention include pharmaceutically acceptable salts, free base or free acid forms of opium alkaloids, semi-synthetic or wholly synthetic opioids.

Pharmaceutically acceptable salts include, but are not limited to:
- metal salts such as sodium salt, potassium salt, secium salt and the like;
- alkaline earth metals such as calcium salt, magnesium salt and the like;
- inorganic acid salts such as hydrochloride, hydrobromide, sulphate, phosphate and the like;
- organic amine salts such as triethylamine salt, pyridine salt, picoline salt, ethanolamine salt, triethanolamine salt, dicyclohexylamine salt, N,N'-dibenzylethylenediamine salt and the like;
- organic acid salts such as methansulfonate, benzenesulfonate, p-toluenesulfonate and the like;
- amino acid salts such as arginate, asparaginate, glutamate and the like.

Examples of opium alkaloids comprise morphine, codeine and thebaine.

Examples of semi-synthetic opiods comprise diamorphine (heroin), oxycodone, hydrocodone, dihydrocodeine, hydromorphone, oxymorphone and nicomorphine.

Examples of wholly synthetic opioids comprise methadone, levomethadyl acetate hydrochloride (LAAM), pethidine (meperidine), ketobemidone, propoxyphene, dextropropoxyphene, dextromoramide, bezitramide, piritramide, pentazocine and phenazocine.

Other opioids are known to one skilled in the art. Preferred opioids in the practice of the present invention are orally bioavailable. More preferred opioids comprise morphine, hydromorphine, hydrocodone, oxymorphone and oxycodone. Other opoids are buprenorphine, hydromorphone, levorphanol, tramadol, tilidine, sufentanil, pentozocine, nalbuphine, meptazinol, meperidine or fentanyl.

In a preferred embodiment of the present invention the pharmaceutical composition may contain only one opioid (opioid agonist) and no other active ingredients.

In another preferred embodiment of the present invention the pharmaceutical composition may contain mixtures of different opioids (opioid agonists). Preferably except from the opioid mixture no further pharmaceutical active ingredients which are not opioids may be included, especially no opioid antagonists may be contained.

In another preferred embodiment of the present invention the pharmaceutical composition may contain a mixture or a combination of one or more opioids (opioid agonists) and one or more opioid antagonists. Preferably only one combination of one opioid and one opioid antagonist may be included. Known mixtures or combinations of opioid agonists and an opioid antagonists are for instance the combinations of pentazocine and naloxone, tilidine and naloxone and morphine and naloxone (see for instance EP 1 810 678 A1 or US 2007/053698).

In another preferred embodiment of the present invention the pharmaceutical composition preferably contains a pharmaceutical active ingredient which is an opioid (opioid agonist) and, if applicable, another pharmaceutical active ingredient, which is not an opioid.

Inert Non-Porous Lubricants

The coating layer may further contain 110 to 250, preferably 140-220% by weight, calculated on dry weight of the polymer mixture, of a non-porous inert lubricant.

Lubricants (sometimes also called glidants) are pharmaceutically acceptable substances which help in preventing agglomeration of polymers during the coating process.

Porous lubricants like silica powders are not suitable for the purposes of the present invention. Porous structures may possibly cause capillary effects that promote the enhanced penetration of the coating by aqueous alcoholic respectively ethanolic media.

Inert means that the lubricant does normally not chemically interact with other substances and is not soluble or only poorly soluble in water and/or ethanol. Not soluble or only poorly soluble means more than 10 parts by weight of solvent required per 1 part by weight of solute. Furthermore inert non-porous lubricants essentially do not influence the glass transition temperature of the polymer mixture of the coating.

Lubricants like glycerol monostearate (GMS), which can not be applied in sufficient amounts to the coating layer to convey resistance against ethanol containing aqueous media are per se not suitable in the sense of the invention. Thus glycerol monostearate (GMS) is not inert in the sense of the invention.

The non-porous inert lubricant may be a layered silica component, a pigment or a stearate compound.

The inert lubricant may be Ca- or Mg-stearate. The inert lubricant may be $TiO_2$.

Most preferred as an inert non-porous lubricant is talc.

Ethanol Resistant Pharmaceutical Formulations

Ethanol resistant pharmaceutical formulations are formulations with release kinetics not significantly affected in the presence of ethanol. Ethanol resistance may be an important registration requirement in the near future. Conventional pharmaceutical coatings, particularly on pellets, are not sufficiently resistant to alcohol. Surprisingly it was found that coatings combining an insoluble and soluble film former provide a higher resistance to alcohol.

An ethanol resistant or sometimes also called rugged formulation is defined by comparing in-vitro release data from testing at 6.8 pH in alcohol free media and equivalent media containing 40% ethanol (details see attachment) and maintaining a difference in release profiles of less than 15% if the release in alcohol free media is less than 20% of the total dose and a difference of less than 30% difference, if the release of the total dose is between 20% and 80%.

OBJECT AND ACHIEVEMENT

The present invention originates from controlled release pharmaceutical forms for oral administration. This type of pharmaceutical form is intended for more or longer-lasting release of active compound, usually during intestinal passage. It is attempted to achieve by means of appropriate formulation of the pharmaceutical form, that, after an initial increase of the concentration of the active compound in the blood level, the blood level shall remain in the therapeutically optimal range as long as possible. Especially too high blood level concentrations of the active compound, which may have toxic effects, should be avoided.

In the case of the release-delaying formulations of oral pharmaceutical forms, the influence of the gastric juice and of the intestinal juices, in particular the ionic strength and the environmental pH, is substantially to be taken into consideration in a manner known per se. A problem exists in that the ideal ratios assumed here for the release of active compound can be altered by the general living habits, thoughtlessness or by addictive behaviour of the patients with respect to the use of ethanol or ethanol-containing drinks. In these cases, the pharmaceutical form which is actually designed for an exclusively aqueous medium is additionally exposed to an ethanol containing medium of greater or lesser strength.

On account of the dissolution of oral delayed-release pharmaceutical forms in alcoholic drinks or simultaneous or overlapping taking thereof with alcoholic drinks, an undesired or even critical acceleration or slowing of the release of active compound can occur. In most cases the presence of ethanol leads to an acceleration of release of the ingredient. So acceleration is the major problem, while slowing is usually less critical. An acceleration or an addition of more than 30% of the release of the pharmaceutical active ingredient absolutely to the release in % without the presence of 40% ethanol must be considered critically.

Since not all patients are aware of the risk of simultaneous taking of a controlled release pharmaceutical form and ethanol-containing drinks or do not follow or are not able to follow appropriate warnings, advice or recommendations, the object is to design oral delayed-release pharmaceutical forms such that their mode of action is affected as little as possible by the presence of ethanol.

The pH-dependent controlled release pharmaceutical composition according to the invention may also be used to reduce the risk of abuse of the included pharmaceutical active ingredient by in-vitro extraction using ethanol containing media before oral ingestion.

The purpose of the present invention is expressively not to stimulate, to promote or to make possible the taking of ethanol-containing drinks together with delayed-release pharmaceutical forms, but to alleviate or to avoid the possibly fatal consequences of intentional or inadvertent abuse. In-vitro means that the extraction takes place out side the human body, for example by extraction of the opioid by addition of high percentage alcoholic drinks like Whiskey or Vodka to the dosage form in a glass.

OBJECT OF THE INVENTION

Because of the not predictability of in-vivo effects, the present invention is based on in-vitro conditions as objectively comprehensible bases of measurement. As a severe test condition in-vitro conditions according to USP Method 1 (basket), 100 rpm buffered at pH 6.8 (European Pharmacopoeia) in a medium with and without the addition to 40% (v/v) ethanol may be chosen.

One object of the invention is solved way when the controlled release pharmaceutical composition fulfils the following conditions:

under conditions according to USP Method 1 (basket), 100 rpm buffered at pH 6.8 (European Pharmacopoeia) where the pharmaceutical active ingredient is released to a degree of less than 20% without the addition of 40% (v/v) ethanol, the difference in the release rate with the addition of 40% (v/v) ethanol shall not be more than plus or minus 15% of the corresponding release value without 40% (v/v) ethanol. For example under conditions where the pharmaceutical active ingredient is released to a degree of 18% without the addition of 40% (v/v) ethanol, the release rate with the addition of 40% (v/v) ethanol shall not differ to more than plus or minus 15% of the release value without 40% (v/v) ethanol, which means that it may be in the range from 3 to 33%.

under conditions according to USP Method 1 (basket), 100 rpm buffered at pH 6.8 (European Pharmacopoeia) where the pharmaceutical active ingredient is released to a degree of 20-80% without the addition of 40% (v/v) ethanol, the difference in the release rate with the addition of 40% (v/v) ethanol shall not be more than plus or minus 30% of the corresponding release value without 40% (v/v) ethanol. For example under conditions where the pharmaceutical active ingredient is released to a degree of 50% without the addition of 40% (v/v) ethanol, the release rate with the addition of 40% (v/v) ethanol shall not differ to more than plus or minus 30% of the release value without 40% (v/v) ethanol, which means that it may be in the range from 20 to 80%.

A controlled release pharmaceutical composition which fulfils this condition can be considered to be resistant against critically accelerated release of the active compound by thoughtlessness or by addictive behaviour of the patients with respect to the use of ethanol or ethanol-containing drinks.

This situation relates essentially to the simultaneous or subsequent consumption of an alcoholic drink together with the taking of the controlled release pharmaceutical form, such that the pharmaceutical form is exposed to a strong ethanol-containing medium in the stomach or intestine.

Measurement Methods

The measurement of the percentage amount of active compound released can be carried out, for example, by on-line UV spectroscopy at a wavelength suitable for the respective active compound. The methodology is familiar to a person skilled in the art.

The release of active compound can be determined according to USP, in particular USP 28-NF23, General Chapter <711>, *Dissolution*, Apparatus 2 (paddle), Method <724>"Delayed Release (Enteric Coated) Articles-General General Drug Release Standard" correct citation needed!, Method B (100 rpm, 37° C.), type I basket, with the following modification: The pharmaceutical forms are first tested at pH 6.8 using a phosphate buffer (European Pharmacopoeia (EP)), which corresponds to an artificial intestinal medium. The measurement in the ethanol containing aqueous medium is carried out using the appropriate amount of 30 or preferably 40% ethanol (v/v) in the medium.

DETAILS OF THE INVENTION

The invention is concerned with

A pH-dependent controlled release pharmaceutical composition, comprising a core, comprising at least one pharmaceutical active ingredient, which is an opioid, wherein the core is coated at least by one coating layer, controlling the release of the pharmaceutical composition, wherein the coating layer comprises a polymer mixture of
i) 40-95, preferably 50-80% by weight of at least one water insoluble essentially neutral vinyl polymer, based on dry weight of the polymer mixture, and
ii) 5-60, preferably 20-50% by weight, based on dry weight of the polymer mixture, of at least one anionic polymer or copolymer, which is insoluble in a buffered medium below pH 4.0 and soluble at least in the range from pH 7.0 to pH 8.0.
characterized in that
the coating layer further contains 110 to 250, preferably 140-220% by weight, calculated on dry weight of the polymer mixture, of a non-porous inert lubricant and the coating is present in an amount of at least 60% by weight calculated on the weight of core.

The Core

In a manner known per se, active ingredient-containing cores or pellet cores form the basis for the coatings of vinyl (co)polymers. Pelletizing can be carried out on active ingredient-free spheres (nonpareills) or core-free pellets, pellet cores, can be produced. First, a rounded, active ingredient-containing substrate with or without a core is produced. By means of a fluidized bed process, liquid can be applied to placebo pellets or other suitable carrier materials, the solvent or suspending agent being evaporated. According to the preparation process, a drying step can be added. The spraying step and subsequently drying may be repeated several times until the intended amount of pharmaceutical active ingredient is fully applied.

The active ingredient is as a rule brought into an organic solvent or into water and mixed. In order to guarantee the satisfactory sprayability of the mixture, it is usually necessary to formulate a mixture with relatively low viscosity. The addition of a detergent, e.g. Tween, in concentrations of 0.1 to 20, preferably 0.5 to 10% by weight, can be advantageous for the reduction of the surface tension. In addition to the active ingredient, they can contain further pharmaceutical excipients: binders, such as cellulose and its derivatives, polyvinylpyrrolidone (PVP), moisture retention agents, disintegration promoters, lubricants, disintegrants, (meth)acrylates, starch and its derivatives, sugar solubilizers or others.

Appropriate application processes are known, for example, from Bauer, Lehmann, Osterwald, Rothgang "Überzogene Arzneiformen" [Coated Pharmaceutical Forms] Wissenschaftliche Verlagsgesellschaft mbH Stuttgart, Chap. 7, pp. 165-196.

Details are furthermore known to the person skilled in the art from textbooks. See, for example:

Voigt, R. (1984): Lehrbuch der pharmazeutischen Technologie [Textbook of Pharmaceutical Technology]; Verlag Chemie Weinheim—Beerfield Beach/Florida—Basle.

Sucker, H., Fuchs, P., Speiser, P.: Pharmazeutische Technologie [Pharmaceutical Technology], George Thieme Verlag Stuttgart (1991), in particular chapters 15 and 16, pp. 626-642.

Gennaro, A., R. (Editor), Remington's Pharmaceutical Sciences, Mack Publishing Co., Easton Pa. (1985), Chapter 88, pp. 1567-1573.

List, P. H. (1982): Arzneiformenlehre [Pharmaceutical Form Theory], Wissenschaftliche Verlagsgesellschaft mbH, Stuttgart.

Pellet cores can be rounded by processes such as rotor agglomeration, precipitation or spray processes, in particular ultrasonic vortex spray processes, to give still uncoated cores or pellet cores of defined size, e.g. 50 to 1000 µm. This has the advantage that the entire core volume is available for active ingredient loading. The active ingredient loading can thereby again be increased in relation to the embodiment having an inert core.

A process of direct compaction may be used to produce cores for mintablets.

Besides the pharmaceutical active ingredient, the core may comprise further pharmaceutical excipients: binders such as cellulose and derivatives thereof, polyvinylpyrrolidone (PVP), humectants, disintegration promoters, lubricants, disintegrants, starch and derivatives thereof, sugar solubilizers or others.

Coating Layer Controlling the Release of the Pharmaceutical Composition

The core is coated at least by one, preferably by one or more preferably by only one coating layer, controlling the release of the pharmaceutical composition. The coating layer conveys the effect of resistance of the release profile against ethanol containing aqueous media. The coating layer, controlling the release of the pharmaceutical composition may also be called an outer coating layer because it surrounds the core.

The (outer) coating layer controls the release of the pharmaceutical composition. The coating layer conveys the effect the resistance of the release profile against ethanol containing aqueous media.

In case of incompatibilities between ingredients of the core and ingredients of the coating an insulating sub coat may be applied between the core and the (outer) coating layer.

The coating layer, controlling the release of the pharmaceutical composition, may be further covered with a non-functional, preferably water soluble top coat that has essentially no influence on the release characteristics.

After preparation of the active ingredient-containing cores or pellet cores, these are provided in spray processes with the coating layer, such that coated cores or coated pellets respectively are obtained. The coating is prepared by means of spray application from organic solution, or preferably from aqueous dispersions. For implementation, it is crucial here that uniform, pore-free coatings result. As a rule, the coated pellets are additionally subsequently dried for a few minutes after the spray application before the conditioning process is begun. As a rule, the polymer coatings contain pharmaceutically customary excipients such as, for example, release agents or plasticizers.

The coating layer, controlling the release of the pharmaceutical composition, is present in an amount of at least 60% by weight, calculated on the weight of core. The coating is preferably present in an amount of 60-200, more preferably 75-180% by weight, calculated on the weight of core.

The amount of the coating may correspond to an average thickness of the coating layer may be in range of about 75-200, preferably in the range of 100-150 µm.

Pellets

The controlled release pharmaceutical composition may preferably be present in the form of coated pellets with an overall average diameter from 100 to 2000, preferably 300 to 1000 µm.

The controlled release pharmaceutical composition according to the invention may be present in the form of coated pellets with an overall average diameter in the range of from 100 to 3000 µm.

The controlled release pharmaceutical composition according to the invention may be present in the form of coated pellets have with an overall average diameter in the range between 100 to 700 µm.

The controlled release pharmaceutical composition according to the invention may be present in the form of coated pellets have with an overall average diameter in the range between 1400 to 3000 µm.

Mini Tablets

The controlled release pharmaceutical composition may preferably be present in the form of coated mini tablets, where the mini tablets have an average diameter from 1 to 3 mm.

Water Insoluble Essentially Neutral Vinyl Polymers or Copolymers

Water-insoluble essentially neutral vinyl polymers or copolymers are understood to mean those polymers or copolymers which are water-insoluble over the entire pH range of 1 to 14 and only swellable in water.

A Vinyl polymer originates from the polymerization of monomers with vinyl groups such like (meth)acrylic monomers.

Essentially neutral is meant in the sense in that the polymers, if at all, may contain only small amounts of ionic groups. Even if small amounts of ionic groups are present the physical-chemical behaviour of such polymers is almost the same as the physical-chemical of polymers without any ionic groups. Essentially neutral is especially meant in the sense in that the polymers contain less than 5, less than 4, less than 3, less than 2 or less than 1% by weight of monomer residues with anionic or cationic side groups. Preferably the water-insoluble neutral vinyl polymers or copolymers do not contain any cationic groups. Most preferably the water-insoluble essentially neutral vinyl polymers or copolymers do not contain any ionic groups at all and thus are neutral water-insoluble vinyl polymers (100% neutral).

Especially water insoluble (meth)acrylic polymers composed of 5 or 10% by weight of monomer residues containing cationic quaternary ammonium groups, e.g. of the type Eudragit® RS or Eudragit® RL, are not suitable for the purposes of the present invention since the resulting pharmaceutical compositions are not sufficiently resistant against the influence of 40% ethanol.

In general, only one or one type of water-insoluble essentially neutral vinyl polymer or copolymer is present in the pharmaceutical composition. However, it is also possible, if appropriate, for two or more water-insoluble polymers or copolymers or types of such polymers or copolymers to be present alongside one another or in a mixture.

Water Insoluble Polymers of the Type of Poly Vinyl Actetate

Suitable water insoluble polymers are of the type of polyvinyl acetate polymers or copolymers derived thereof.

Examples of water insoluble poly vinyl acetate type polymers or copolymers are polyvinyl acetate (PVAc, Kollicoat), vinylacetate-vinylpyrrolidon-copolymer (Kollidon® VA64).

Water Insoluble (meth)acrylic Copolymers

Among the Water insoluble (meth)acrylic copolymers neutral or essentially neutral methacrylate copolymers are suitable for purposes of the present invention.

Neutral (meth)acrylate Copolymers (EUDRAGIT® NE Type EUDRAGIT® NM Type)

Neutral or essentially neutral methacrylate copolymers consist at least to an extent of more than 95% by weight, in particular to an extent of at least 98% by weight, preferably to an extent of at least 99% by weight, in particular to an extent of at least 99% by weight, more preferably to an extent of 100% by weight, of (meth)acrylate monomers with neutral radicals, especially $C_1$- to $C_4$-alkyl radicals.

Suitable (meth)acrylate monomers with neutral radicals are, for example, methyl methacrylate, ethyl methacrylate, butyl methacrylate, methyl acrylate, ethyl acrylate, butyl acrylate. Preference is given to methyl methacrylate, ethyl acrylate and methyl acrylate.

Methacrylate monomers with anionic radicals, for example acrylic acid and/or methacrylic acid, may be present in small amounts of less than 5% by weight, preferably not more than 2% by weight, more preferably not more than 1 or 0.05 to 1% by weight.

Suitable examples are neutral or virtually neutral (meth)acrylate copolymers composed of 20 to 40% by weight of ethyl acrylate, 60 to 80% by weight of methyl methacrylate and 0 to less than 5% by weight, preferably 0 to 2 or 0.05 to 1% by weight of acrylic acid or methacrylic acid (EUDRAGIT® NE or Eudragit® NM type).

EUDRAGIT® NE and Eudragit® NM are copolymers composed of free-radically polymerized units of 30% by weight of ethyl acrylate and 70% by weight of methyl methacrylate.

Preference is given to neutral or essentially neutral methyl acrylate copolymers which, according to WO 01/68767, have been prepared as dispersions using 1-10% by weight of a nonionic emulsifier having an HLB value of 15.2 to 17.3. The latter offer the advantage that there is no phase separation with formation of crystal structures by the emulsifier (Eudragit® NM type).

According to EP 1 571 164 A2, corresponding, virtually neutral (meth)acrylate copolymers with small proportions of 0.05 to 1% by weight of mono olefinically unsaturated $C_3$-$C_8$-carboxylic acids can, however, also be prepared by emulsion polymerization in the presence of comparatively small amounts of anionic emulsifiers, for example 0.001 to 1% by weight.

A suitable water insoluble polymer is a copolymer composed of free-radical polymerized units of more than 95 up to 100% by weight $C_1$- to $C_4$-alkyl esters of acrylic or of methacrylic acid and less than 5% by weight of acrylic or methacrylic acid.

Water Soluble Anionic Polymers

A water soluble anionic polymer in the sense of the present invention is a polymer which is insoluble below pH 5.0 and soluble at least in the range from pH 7.0 to pH 8.0, preferably in the range from pH 6.0 to 8.0, most preferably soluble in the range from 5.5 to 8.0 in a suitable buffered medium, preferably a buffered medium according to USP or European Pharmacopoeia standards. Most of the polymers which are soluble in the range from pH 7.0 to pH 8.0 in a suitable buffered aqueous medium are not soluble in pure water or demineralised water.

Water Soluble Anionic Cellulose Derivatives

Anionic cellulose derivates are based on a natural cellulose chain and chemically modified with anionic compounds. The polymer may by partially or totally neutralized, preferably with alkali ions. Examples of anionic cellulose derivatives are cellulose acetate phthalate (CAP), hydroxy propyl methyl cellulose phthalate (HPMCP), carboxy methyl cellulose (CMC), hydroxyl propyl methyl cellulose acetate succinate (HPMCAS) or cellulose acetate succinate (CAS).

Water Soluble Anionic (meth)acrylate Copolymers

A suitable water soluble anionic (meth)acrylate copolymer is composed of free-radical polymerized units of 25 to 95, preferably 40 to 95, in particular 60 to 40, % by weight free-radical polymerized $C_1$- to $C_4$-alkyl esters of acrylic or of methacrylic acid and 75 to 5, preferably 60 to 5, in particular 40 to 60, % by weight (meth)acrylate monomers having an anionic group.

The proportions mentioned normally add up to 100% by weight. However it is also possible in addition, without this leading to an impairment or alteration of the essential properties of the invention, for small amounts in the region of up to 10 or 0 to 10, for example 1 to 5, % by weight of further monomers capable of vinylic copolymerization, such as, for example, hydroxyethyl methacrylate or hydroxyethyl acrylate, to be present. However, it is preferred that no further monomers capable of vinylic copolymerization are present. It is generally preferred that no further monomers except from those explicitly mentioned are present in the water soluble anionic (meth)acrylate copolymers.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group is, for example, acrylic acid, with preference for methacrylic acid.

Suitable anionic (meth)acrylate copolymers are those composed of 40 to 60% by weight methacrylic acid and 60 to 40% by weight methyl methacrylate or 60 to 40% by weight ethyl acrylate (EUDRAGIT® L or EUDRAGIT® L 100-55 types).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L 30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer polymerized out of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
  20 to 34% by weight methacrylic acid and/or acrylic acid,
  20 to 69% by weight methyl acrylate and
  0 to 40% by weight ethyl acrylate and/or where appropriate
  0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable is a copolymer composed of
  20 to 33% by weight methacrylic acid and/or acrylic acid,
  5 to 30% by weight methyl acrylate and
  20 to 40% by weight ethyl acrylate and
  more than 10 to 30% by weight butyl methacrylate and where appropriate 0 to 10% by weight further monomers capable of vinylic copolymerization, where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of
  20 to 33, preferably 25 to 32, particularly preferably 28 to 31% by weight methacrylic acid or acrylic acid, with preference for methacrylic acid,
  5 to 30, preferably 10 to 28, particularly preferably 15 to 25% by weight methyl acrylate,
  20 to 40, preferably 25 to 35, particularly preferably 18 to 22% by weight ethyl acrylate, and
  more than 10 to 30, preferably 15 to 25, particularly preferably 18 to 22% by weight butyl methacrylate,
where the monomer composition is chosen, so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

Preparation of Anionic (meth)acrylate Copolymers

The anionic (meth)acrylate copolymers can be prepared in a manner known per se by free-radical polymerization of the monomers (see, for example, EP 0 704 207 A2 and EP 0 704 208 A2). The copolymer according to the invention can be prepared in a manner known per se by free-radical emulsion polymerization in aqueous phase in the presence of, preferably, anionic emulsifiers, for example by the process described in DE-C 2 135 073.

The copolymer can be prepared by conventional processes of free-radical polymerization continuously or discontinuously (batch processes) in the presence of free-radical forming initiators and, where appropriate, regulators to adjust the molecular weight undiluted, in solution, by bead polymerization or in emulsion. The average molecular weight Mw (weight average, determined for example by measuring the solution viscosity) may be for example in the range from 80 000 to 1 000 000 (g/mol). Emulsion polymerization in aqueous phase in the presence of water-soluble initiators and (preferably anionic) emulsifiers is preferred.

In the case of bulk polymerization, the copolymer can be obtained in solid form by crushing, extrusion, granulation or hot cut.

The (meth)acrylate copolymers are obtained in a manner known per se by free-radical bulk, solution, bead or emulsion polymerization. They must be brought before processing to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled person, e.g. air jet mills, pinned disc mills, compartment mills. It is possible where appropriate to include appropriate sieving steps. A suitable mill for industrial large quantities is, for example, an opposed jet mill (Multi No. 4200) operated with a gauge pressure of about 6 bar.

Partial Neutralization

The anionic polymers may be partially or fully neutralized by bases. Bases suitable are those expressly mentioned in EP 0 088 951 A2 or WO 2004/096185 or derivable there from. In particular: sodium hydroxide solution, potassium hydroxide solution (KOH), ammonium hydroxide or organic bases such as, for example, triethanolamine, sodium carbonate, potassium carbonate, sodium bicarbonate, trisodium phosphate, trisodium citrate or ammonia or physiologically tolerated amines such as triethanolamine or tris(hydroxymethyl)aminomethane. Further suitable cationic, organic bases are basic amino acids histidine, arginine and/or lysine.

Multiparticulate Pharmaceutical Forms

The controlled release pharmaceutical composition according to the invention may have the form of pellets, which are contained in a multiparticulate pharmaceutical form, for instance in the form of a compressed tablet, capsules, sachets, effervescent tablets or reconstitutable powders.

Top Coat and Sub Coats

The controlled release pharmaceutical composition according to the invention may be further coated with a sub coat and/or a top coat.

A sub coat may be located between the core and the coating layer controlling the release of the pharmaceutical active substance (controlling layer). A sub coat may have the function to separate substances of the core from substances of the controlling layer which may be incompatible with each other. The sub coat has essentially no influence on the release characteristics. A sub coat is preferably essentially water-soluble, for instance it may consist of substances like hydroxyl propyl methyl cellulose (HPMC) as a film former. The average thickness of the sub coat layer is very thin, for example not more than 15 μm, preferably not more than 10 μm.

A top coat is also preferably essentially water soluble. A top coat may have the function of colouring the pharmaceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical excipients like pigments or lubricants in small amounts. The topcoat has essentially no influence on the release characteristics.

The expressions sub coat and top coat is well known to the person skilled in the art.

Process for Producing a Pharmaceutical Form According to the Invention

The controlled release pharmaceutical composition according to the invention may be produced in a manner known per se by pharmaceutically customary processes such as direct compression, compression of dry, wet or sintered granules and subsequent rounding off, wet or dry granulation or direct pelleting or by binding powders (powder layering) onto active ingredient-free beads or neutral cores (nonpareilles) or active ingredient-containing particles and by applying the polymer coating in a spray process or by fluidized bed granulation.

Excipients/Customary Additives

The core may further contain, beside the pharmaceutical active ingredient, excipients or customary additives respectively in a manner known to the person skilled in the art.

The coating layer may also, beside the polymer mixture and the non-porous inert lubricant as essential ingredients, further contain excipients or customary additives respectively in a manner known to the person skilled in the art.

Excipients or customary additives respectively shall be added only at amounts which do not negatively influence the function of the core and the out coating layer according to the invention as disclosed in here. As a guide line excipients or customary additives may be for instance used in a way similar or identical as in the working examples disclosed in here.

Excipients customary in pharmacy, occasionally also referred to as customary additives, are added to the formulation of the invention, preferably during production of the granules or powders. It is, of course, always necessary for all the excipients or customary additives employed to be toxicologically acceptable and usable in particular in medicaments without a risk for patients.

The amounts employed and the use of excipients customary in pharmacy for medicament coatings or layerings are familiar to the skilled worker. Examples of possible excipients or additives customary in pharmacy are release agents, pigments, stabilizers, antioxidants, pore formers, penetration promoters, gloss agents, aromatizing substances or flavourings. They serve as processing aids and are intended to ensure a reliable and reproducible production process and good long-term storage stability or they achieve additional advantageous properties in the pharmaceutical form. They are added to the polymer preparations before processing and may influence the permeability of the coatings, it being possible to utilize this where appropriate as additional control parameter.

Pigments:

If pigments are additionally present they are preferably added to the top coat. Pigments incompatible with the coating agent are in particular those pigments which, may be added directly to a dispersion, e.g. by stirring in, in the usual amounts used of, for example, 20 to 400% by weight based on the dry weight of the (meth)acrylate copolymer, lead to destabilization of the dispersion, coagulation, to signs of inhomogeneity or similarly unwanted effects. The pigments to be used are moreover of course non-toxic and suitable for pharmaceutical purposes. Concerning this, see also, for example: Deutsche Forschungsgemeinschaft, *Farbstoffe für Lebensmittel*, Harald, Boldt Verlag KG, Boppard (1978); Deutsche Lebensmittelrundschau 74, No. 4, p. 156 (1978); Arzneimittelfarbstoffverordnung AmFarbV of 25 Aug. 1980.

Pigments incompatible with the coating agent may be for example alumina pigments. Examples of incompatible pigments are orange yellow, cochineal red lake, coloured pigments based on alumina or azo dyes, sulphonic acid dyes, orange yellow S (E110, C.I. 15985, FD&C Yellow 6), indigo carmine (E132, C.I. 73015, FD&C Blue 2), tartrazine (E 102, C.I. 19140, FD&C Yellow 5), Ponceau 4R (E 125, C.I. 16255, FD&C Cochineal Red A), quinoline yellow (E 104, C.I. 47005, FD&C Yellow 10), erythrosine (E127, C.I. 45430, FD&C Red 3), azorubine (E 122, C.I. 14720, FD&C Carmoisine), amaranth (E 123, C.I. 16185, FD&C Red 2), acid brilliant green (E 142, C.I. 44090, FD&C Green S).

The E numbers indicated for the pigments relate to an EU numbering. Concerning this, see also "Deutsche Forschungsgemeinschaft, Farbstoffe für Lebensmittel, Harald Boldt Verlag KG, Boppard (1978); Deutsche Lebensmittelrundschau 74, No. 4, p. 156 (1978); Arzneimittelfarbstoffverordnung AmFarbV of 25 Aug. 1980. The FD&C numbers relate to the approval in food, drugs and cosmetics by the U.S. food and drug administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Plasticizers

Further additives may also be plasticizers. Plasticizers may be favourably added to the coating layer. The usual amounts are between 0 and 50, preferably 5 to 20, % by weight based for example on the (meth)acrylate copolymer of the layer coating layer.

Plasticizers may influence the functionality of the polymer layer, depending on the type (lipophilic or hydrophilic) and added amount. Plasticizers achieve through physical interaction with the polymers a reduction in the glass transition temperature and promote film formation, depending on the added amount. Suitable substances usually have a molecular weight of between 100 and 20 000 and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate and polyethylene glycols 200 to 12 000. Preferred plasticizers are triethyl citrate (TEC), acetyl triethyl citrate (ATEC) and dibutyl sebacate (DBS). Mention should additionally be made of esters which are usually liquid at room temperature, such as citrates, phthalates, sebacates or castor oil. Esters of citric acid and sebacinic acid are preferably used.

Addition of the plasticizers to the formulation can be carried out in a known manner, directly, in aqueous solution or after thermal pre-treatment of the mixture. It is also possible to employ mixtures of plasticizers.

Use

The pH-dependent controlled release pharmaceutical composition according to the invention may be used to reduce the risk of enhanced release of the included pharmaceutical active ingredient after oral ingestion by simultaneous or subsequent consumption of ethanol containing drinks (misuse).

The pH-dependent controlled release pharmaceutical composition according to the invention may be used to reduce the risk of abuse of the included pharmaceutical active ingredient by in-vitro extraction using ethanol containing media before oral ingestion.

EXAMPLES

Methods
Model Drug

Studies were conducted using Morphine sulphate as a model drug.

Micronised talc was used as an excipient.
Dissolution Studies

Coated pellets were tested according to
USP 28-NF23, General Chapter <711>, *Dissolution*,
Dissolution Parameters:
  Apparatus: USP Type-I (Basket)
  RPM: 100/min.
  Temperature: 37.5±0.5° C.
  Dissolution volume: 500 ml.
  Withdrawal volume: 5 ml withdrawn manually using pipette, without replenishment of the medium.
  Withdrawal interval: 1.0 Hr, 2.0 Hr, 3.0 Hr, 4.0 Hr, 5.0 Hr, 6.0 Hr, 7.0 Hr, 8.0 Hr, 9.0 Hr, 10.0 Hr, 11.0 Hr and 12.0 Hr.
  Mode of detection: HPLC
Dissolution Medium 1:
  Phosphate buffered saline pH 6.8 (European Pharmacopoeia=EP)
Dissolution Medium 2:
  Phosphate buffered saline pH 6.8, EP with 30% v/v alcohol-0.9 g of $KH_2PO_4$, 1.8 g of $K_2HPO_4$, 7.65 g of NaCl with 630 ml D.M. water and 270 ml of alcohol.
Dissolution Medium 3:
  Phosphate buffered saline pH 6.8, EP with 40% v/v alcohol-0.9 g of $KH_2PO_4$, 1.8 g of $K_2HPO_4$, 7.65 g of NaCl with 540 ml D.M. water and 360 ml of alcohol.
Copolymers EUDRAGIT® NE is a copolymer composed of free-radically polymerized units of 30% by weight of ethyl acrylate and 70% by weight of methyl methacrylate.

EUDRAGIT® FS is a copolymer composed of free-radically polymerized units of 25% by weight methyl methacrylate, 65% by weight methyl acrylate and 10% by weight methacrylic acid.

EUDRAGIT® L 100-55 is a copolymer composed of free-radically polymerized units of 50% by weight ethyl acrylate and 50% by weight methacrylic acid.

Formulation Details

Cores (sugar sphere etc.) of 400-600 microns were loaded with Morphine sulphate pentahydrate in a fluidised bed processor using bottom spray. Polyvinyl pyrrolidone was used as a binder.

Coating Suspension Preparation:

EUDRAGIT® dispersions are mixed in a suitable vessel applying gentle stirring. Lubricants and different polymers are dissolved or dispersed in water applying high shear forces.

The lubricant suspension is poured into the EUDRAGIT® dispersion applying gentle stirring. Stirring is continued through the entire coating process.

Coating Process:

300 g drug layered pellets were coated with different coating suspensions in a fluidized bed apparatus under appropriate conditions, i.e. a spray rate of approximately 20 g/min coating suspension per kg cores and a bed temperature of approximately 25-28° C. After coating the pellets were fluidised at 50° C. for one hour in a fluid bed processor.

Example 1

Comparative Example

EUDRAGIT® NE 30 D/Talc (200% w/w of the Polymer)/ 90% w/w Weight Gain by Coating Layer
Formulation Details of Coating Suspension for 300 g of Cores:

| Function | Ingredients | Quantity in g | Solids in g |
|---|---|---|---|
| Insoluble polymer | EUDRAGIT ® NE 30 D | 300 | 90 |
| Soluble polymer | — | — | — |
| Lubricant | Talc | 180 | 180 |
| Diluent | Water, purified | 1320 | — |

Procedure:

300 g Morphine sulphate pellets were coated with EUDRAGIT® NE 30 D at 90% w/w level with 200% w/w talc as an inert non-porous lubricant in the coating suspension. The coating was carried out in fluid bed processor using normal process parameters.

Dissolution Results:

Comparative release profiles in phosphate buffered saline pH 6.8, EP and corresponding alcoholic medium with 30% v/v alcohol.

|  | Drug Release in % | |
|---|---|---|
| Time in (hours) | without EtOH | with 30% (v/v) EtOH |
| 0 | 0.00 | 0.00 |
| 1 | 0.01 | 4.24 |
| 2 | 0.20 | 8.52 |
| 3 | 2.52 | 16.84 |
| 4 | 4.11 | 20.35 |
| 5 | 8.58 | 29.38 |
| 6 | 12.32 | 36.30 |
| 7 | 18.58 | 58.88 |
| 8 | 22.21 | 65.86 |
| 9 | 28.54 | 69.86 |
| 10 | 40.98 | 74.43 |
| 11 | 58.21 | 78.00 |
| 12 | 60.23 | 80.01 |

Inference:

The coated pellets failed to show resistance at even 30% v/v level of alcohol and are therefore not expected to be resistant against 40% ethanol hence no inventive polymer combination was applied.

Example 2

Comparative Example

EUDRAGIT® NE 30 D-HPMC (94:6)/Talc (200% w/w of the Polymer)/105% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT® NE 30 D | 333 | 100 |
| Soluble polymer | HPMC, 5 cps | 6 | 6 |
| Lubricant | Talc | 210 | 210 |
| Diluent | Water, purified | 1552 | |

Procedure:

Morphine sulphate pellets were coated with hydroxypropyl methyl cellulose (HPMC), 5 cps in combination with EUDRAGIT® NE 30 D with 200% w/w talc as an inert non-porous lubricant in the coating suspension. The ratio of EUDRAGIT® NE 30 D dry substance to hydroxyl propyl methyl cellulose was 94.3%:5.7%. The coating was carried out in fluid bed processor using normal process parameters.

Dissolution Results:

Comparative release profiles in phosphate buffered saline pH 6.8, (Eur. Pharm.) and corresponding alcoholic medium with 30% v/v alcohol.

| Time in Hr. | % Drug Release | |
|---|---|---|
|  | without EtOH | with 30% (v/v) EtOH |
| 0.00 | 0.00 | 0.00 |
| 1.00 | 0.06 | 5.06 |
| 2.00 | 8.32 | 22.64 |
| 3.00 | 14.54 | 37.86 |
| 4.00 | 18.87 | 50.11 |
| 5.00 | 28.21 | 65.01 |
| 6.00 | 36.56 | 72.54 |
| 7.00 | 46.25 | 81.55 |
| 8.00 | 57.68 | 87.33 |
| 9.00 | 67.45 | 91.77 |
| 10.00 | 75.58 | 94.03 |
| 11.00 | 81.56 | 97.43 |
| 12.00 | 84.68 | 100.00 |

Inference:

The coated pellets failed to show resistance at even 30% v/v level of alcohol and are therefore not expected to be resistant against 40% ethanol hence the water soluble polymer (HPMC) is not anionic but neutral.

Example 3

Comparative Example

EUDRAGIT® NE 30 D/EUDRAGIT® FS 30 D (1:9)/Talc (200% w/w of the Polymer)/105% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT® NE 30D | 35 | 10.5 |
| Soluble polymer | EUDRAGIT® FS 30D | 315 | 94.5 |
| Lubricant | Talc | 210 | 210 |
| Diluent | Water, purified | 1540 | |

Procedure:

Morphine sulphate pellets were coated with a mixture of EUDRAGIT® NE 30 D and EUDRAGIT® FS 30 D using 200% w/w talc as an inert non-porous lubricant in the coating suspension. The ratio of EUDRAGIT® NE 30 D dry substance and EUDRAGIT® FS 30 D dry substance was 10%:90%. The coating was carried out in fluid bed processor using normal process parameters.

Dissolution Results:

Comparative release profiles in phosphate buffered saline pH 6.8, EP and corresponding alcoholic medium with 30% v/v alcohol.

| Time in Hr. | % Drug Release | |
|---|---|---|
|  | without EtOH | with 30% (v/v) EtOH |
| 0.00 | 0.00 | 0.00 |
| 1.00 | 3.65 | 6.98 |
| 2.00 | 20.02 | 62.32 |
| 3.00 | 41.23 | 82.37 |
| 4.00 | 66.65 | 96.32 |
| 5.00 | 85.36 | 99.06 |
| 6.00 | 92.65 | 100.00 |
| 7.00 | 99.20 | |
| 8.00 | 100.00 | |

Inference:

The coated pellets failed to show resistance at even 30% v/v level of alcohol and are therefore not expected to be resistant against 40% ethanol, hence concentration of the neutral methacrylate copolymer was too low.

Example 4

Comparative Example

EUDRAGIT® NE 30D/EUDRAGIT® FS 30D (5.5:4.5)/Talc (100% w/w of the Polymer)/70% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT ® NE 30 D | 193 | 58 |
| Soluble polymer | EUDRAGIT ® FS 30 D | 157 | 47 |
| Lubricant | Talc | 105 | 105 |
| Diluent | Water, purified | 945 | — |

Procedure:

Morphine sulphate pellets were coated with a mixture of EUDRAGIT® NE 30 D and EUDRAGIT® FS 30 D using 100% w/w of talc as an inert non-porous lubricant in coating suspension. The ratio of EUDRAGIT® NE 30 D dry substance and EUDRAGIT® FS 30 D dry substance was 55%:45%. The coating was carried out in fluid bed processor using normal process parameters.

Dissolution Results:

Comparative release profiles in phosphate buffered saline pH 6.8, EP and corresponding alcoholic medium with 40% v/v alcohol.

| | % Drug Release | |
|---|---|---|
| Time in Hr. | without EtOH | with 40% (v/v) EtOH |
| 0.00 | 0 | 0.00 |
| 1.00 | 2.23 | 21.18 |
| 2.00 | 20.20 | 56.09 |
| 3.00 | 44.00 | 82.21 |
| 4.00 | 60.20 | 91.56 |
| 5.00 | 70.90 | 96.21 |
| 6.00 | 79.80 | 98.30 |
| 7.00 | 88.21 | 100.00 |
| 8.00 | 95.32 | |
| 9.00 | 98.21 | |
| 10.00 | 100.00 | |

Inference:

The coated pellets failed to show resistance in 40% v/v level of alcohol hence the level of the non-porous inert lubricant was too low.

Example 5

Comparative Example

EUDRAGIT® NE 30 D/EUDRAGIT® L 30 D-55 (7:3)/Talc (150% w/w of the Polymer)/50% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT ® NE 30D | 140 | 42 |
| Soluble polymer | EUDRAGIT ® L 30D-55 | 60 | 18 |
| Lubricant | Talc | 90 | 90 |
| Diluent | Water, purified | 860 | — |

Procedure:

Morphine sulphate pellets were coated with combination of EUDRAGIT® NE and EUDRAGIT® L 30 D-55 using 150% w/w of talc as an inert non-porous lubricant in coating suspension. The ratio of EUDRAGIT® NE 30 D dry substance and EUDRAGIT® L 30 D-55 dry substance (=EUDRAGIT® L 100-55) was 70%:30%. The coating was carried out in fluid bed processor using normal process parameters.

Dissolution Results:

Comparative release profiles in phosphate buffered saline pH 6.8, EP and corresponding alcoholic medium with 40% v/v alcohol.

| | % Drug Release | |
|---|---|---|
| Time in Hr. | without EtOH | with 40% (v/v) EtOH |
| 0.00 | 0 | 0 |
| 1.00 | 5.67 | 10.04 |
| 2.00 | 24.13 | 52.76 |
| 3.00 | 42.78 | 76.05 |
| 4.00 | 55.67 | 92.31 |
| 5.00 | 60.83 | 97.82 |
| 6.00 | 81.07 | 100.00 |
| 7.00 | 91.24 | |
| 8.00 | 97.58 | |
| 9.00 | 100.00 | |

Inference:

The coated pellets failed to show resistance in 40% v/v level of alcohol hence the coating level was too low.

Example 6

Comparative Example

EUDRAGIT® NE 30 D/EUDRAGIT® L 30 D-55 (3.5:6.5)/Talc (200% w/w of the Polymer)/105% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT ® NE 30 D | 123 | 37 |
| Soluble polymer | EUDRAGIT ® L 30 D-55 | 227 | 68 |

-continued

| Function | Ingredients | Quantity in g | Solids in g |
|---|---|---|---|
| Lubricant | Talc | 210 | 210 |
| Diluent | Water, purified | 1540 | — |

Procedure:

Morphine sulphate pellets were coated with combination of EUDRAGIT® NE and EUDRAGIT® L 30 D-55 using 200% w/w of talc as an inert non-porous lubricant in coating suspension. The ratio of EUDRAGIT® NE 30 D dry substance and EUDRAGIT® L 30 D-55 dry substance (=EUDRAGIT® L 100-55) was 35%:65%. The coating was carried out in fluid bed processor using normal process parameters.

Dissolution Results:

Comparative release profiles in phosphate buffered saline pH 6.8, EP and corresponding alcoholic medium with 40% v/v alcohol.

| | % Drug Release | |
|---|---|---|
| Time in Hr. | without EtOH | with 40% (v/v) EtOH |
| 0.00 | 0.00 | 0.00 |
| 1.00 | 5.67 | 12.21 |
| 2.00 | 24.13 | 51.09 |
| 3.00 | 40.78 | 77.34 |
| 4.00 | 54.01 | 93.72 |
| 5.00 | 66.83 | 100.00 |
| 6.00 | 79.89 | |
| 7.00 | 91.24 | |
| 8.00 | 97.58 | |
| 9.00 | 100.00 | |

Inference:

The coated pellets failed to show resistance in 40% v/v level of alcohol hence the level of the insoluble polymer EUDRAGIT® NE 30 D was too low.

Example 7

EUDRAGIT® NE 30 D/EUDRAGIT® FS 30D (8:2)/Talc (200% w/w of the Polymer)/105% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT ® NE 30D | 280 | 84 |
| Soluble polymer | EUDRAGIT ® FS 30D | 70 | 21 |
| Lubricant | Talc | 210 | 210 |
| Diluent | Water, purified | 1540 | — |

Procedure:

Morphine sulphate pellets were coated with combination of EUDRAGIT® NE and EUDRAGIT® FS using 100% w/w of talc as an inert non-porous lubricant in coating suspension. The ratio of EUDRAGIT® NE 30 D dry substance and EUDRAGIT® FS 30 D dry substance was 80%:20%. The coating was carried out in fluid bed processor using normal process parameters.

Dissolution Results:

Comparative release profiles in phosphate buffered saline pH 6.8, EP and corresponding alcoholic medium with 30% v/v alcohol.

| | % Drug Release | |
|---|---|---|
| Time in Hr. | without EtOH | with 30% (v/v) EtOH |
| 0.00 | 0 | 0.00 |
| 1.00 | 2.23 | 1.50 |
| 2.00 | 5.39 | 2.12 |
| 3.00 | 8.45 | 4.68 |
| 4.00 | 11.36 | 5.98 |
| 5.00 | 16.36 | 8.35 |
| 6.00 | 23.78 | 12.98 |
| 7.00 | 32.57 | 20.45 |
| 8.00 | 44.89 | 31.29 |
| 9.00 | 58.45 | 41.36 |
| 10.00 | 69.35 | 52.45 |
| 11.00 | 78.65 | 63.78 |
| 12.00 | 83.60 | 74.60 |

Inference:

Values of the release profiles of the coated pellets tested in 30% v/v hydro-alcoholic dissolution medium were resistant when compared with the release profiles of the coated pellets tested in dissolution medium without alcohol for all the time points.

Comparative release profiles in phosphate buffered saline pH 6.8, EP and corresponding alcoholic medium with 40% v/v alcohol.

| | % Drug Release | |
|---|---|---|
| Time in Hr. | without EtOH | with 40% (v/v) EtOH |
| 0.00 | 0 | 0.00 |
| 1.00 | 2.23 | 1.25 |
| 2.00 | 5.39 | 1.96 |
| 3.00 | 8.45 | 3.98 |
| 4.00 | 11.36 | 4.56 |
| 5.00 | 16.36 | 7.98 |
| 6.00 | 23.78 | 10.25 |
| 7.00 | 32.57 | 16.98 |
| 8.00 | 44.89 | 25.45 |
| 9.00 | 58.45 | 38.54 |
| 10.00 | 69.35 | 48.69 |
| 11.00 | 78.65 | 59.45 |
| 12.00 | 83.60 | 70.87 |

Inference:

Values of the release profiles of the coated pellets tested in 40% v/v hydro-alcoholic dissolution medium were resistant when compared with the release profiles of the coated pellets tested in dissolution medium without alcohol for all the time points.

Example 8

EUDRAGIT® NE 30 D/EUDRAGIT® FS 30 D (7:3)/Talc (200% w/w of the Polymer)/105% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT ® NE 30D | 247 | 74 |
| Soluble polymer | EUDRAGIT ® FS 30D | 103 | 31 |

-continued

| Function | Ingredients | Quantity in g | Solids in g |
|---|---|---|---|
| Lubricant | Talc | 210 | 210 |
| Diluent | Water, purified | 1540 | |

Procedure:

Morphine sulphate pellets were coated with combination of EUDRAGIT® NE and EUDRAGIT® FS using 200% w/w of talc as an inert non-porous lubricant in coating suspension. The ratio of EUDRAGIT® NE 30 D dry substance and EUDRAGIT® FS 30 D dry substance was 70%:30%. The coating was carried out in fluid bed processor using normal process parameters.

Dissolution Results:

Comparative release profiles in phosphate buffered saline pH 6.8, EP and corresponding alcoholic medium with 30% v/v alcohol.

| | % Drug Release | |
|---|---|---|
| Time in Hr. | without EtOH | with 30% (v/v) EtOH |
| 0.00 | 0 | 0 |
| 1.00 | 2.23 | 0 |
| 2.00 | 15.39 | 9.57 |
| 3.00 | 32.45 | 24.69 |
| 4.00 | 45.23 | 35.45 |
| 5.00 | 56.78 | 49.23 |
| 6.00 | 69.78 | 58.32 |
| 7.00 | 79.12 | 70.30 |
| 8.00 | 86.21 | 79.54 |
| 9.00 | 95.23 | 88.15 |
| 10.00 | 99.69 | 94.32 |
| 11.00 | 100.00 | 99.01 |

Inference:

Values of the release profiles of the coated pellets tested in 30% v/v hydro-alcoholic dissolution medium were resistant when compared with the release profiles of the coated pellets tested in dissolution medium with out alcohol for all the time points.

Comparative release profiles in phosphate buffered saline pH 6.8, EP and corresponding alcoholic medium with 40% v/v alcohol.

| | % Drug Release | |
|---|---|---|
| Time in Hr. | without EtOH | with 40% (v/v) EtOH |
| 0.00 | 0 | 0 |
| 1.00 | 2.23 | 7.84 |
| 2.00 | 15.39 | 21.56 |
| 3.00 | 32.45 | 39.45 |
| 4.00 | 45.23 | 51.65 |
| 5.00 | 56.78 | 64.32 |
| 6.00 | 69.78 | 78.65 |
| 7.00 | 79.12 | 89.32 |
| 8.00 | 86.21 | 97.12 |
| 9.00 | 95.23 | 100.00 |
| 10.00 | 99.69 | |
| 11.00 | 100.00 | |

Inference:

Values of the release profiles of the coated pellets tested in 40% v/v hydro-alcoholic dissolution medium were resistant when compared with the release profiles of the coated pellets tested in dissolution medium without alcohol for all the time points.

Example 9

EUDRAGIT® NE 30 D/EUDRAGIT® FS 30 D (5.5:4.5)/Talc (200% w/w of the Polymer)/105% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT ® NE 30D | 193 | 57.75 |
| Soluble polymer | EUDRAGIT ® FS 30D | 158 | 47.25 |
| Lubricant | Talc | 210 | 210 |
| Diluent | Water, purified | 1540 | — |

Procedure:

Morphine sulphate pellets were coated with combination of EUDRAGIT® NE and EUDRAGIT® FS using 200% w/w of talc as an inert non-porous lubricant in coating suspension. The ratio of EUDRAGIT® NE 30 D dry substance and EUDRAGIT® FS 30 D dry substance was 55%:45%. The coating was carried out in fluid bed processor using normal process parameters.

Dissolution Results:

Comparative release profiles in phosphate buffered saline pH 6.8, EP and corresponding alcoholic medium with 30% v/v alcohol.

| | % Drug Release | |
|---|---|---|
| Time in Hr. | without EtOH | with 30% (v/v) EtOH |
| 0.00 | 0.00 | 0.00 |
| 1.00 | 0.40 | 7.40 |
| 2.00 | 27.20 | 27.60 |
| 3.00 | 58.00 | 48.70 |
| 4.00 | 80.20 | 65.10 |
| 5.00 | 92.90 | 85.10 |
| 6.00 | 99.80 | 98.10 |
| 7.00 | 100.00 | 100.00 |

Inference:

Values of the release profiles of the coated pellets tested in 30% v/v hydro-alcoholic dissolution medium were resistant when compared with the release profiles of the coated pellets tested in dissolution medium without alcohol for all the time points.

Comparative release profiles in phosphate buffered saline pH 6.8, EP and corresponding alcoholic medium with 40% v/v alcohol.

| | % Drug Release | |
|---|---|---|
| Time in Hr. | without EtOH | with 40% (v/v) EtOH |
| 0.00 | 0.00 | 0.00 |
| 1.00 | 0.40 | 8.30 |
| 2.00 | 27.20 | 25.50 |
| 3.00 | 58.00 | 46.00 |
| 4.00 | 80.20 | 66.60 |
| 5.00 | 92.90 | 87.10 |

-continued

| Time in Hr. | % Drug Release | |
|---|---|---|
| | without EtOH | with 40% (v/v) EtOH |
| 6.00 | 99.80 | 98.80 |
| 7.00 | 100.00 | 100.00 |

Inference:

Values of the release profiles of the coated pellets tested in 40% v/v hydro-alcoholic dissolution medium were resistant when compared with the release profiles of the coated pellets tested in dissolution medium without alcohol for all the time points.

Dissolution Studies to Show pH Dependency

The pH Dependency of Alcohol Resistance Formulation and their Resistance in Alcoholic Dissolution Medium with Different pH Shall be Demonstrated.

(1) The formulation in Example 9 was analysed in 0.1 N HCl, USP (pH=1.2) for 2 hours and its corresponding alcoholic medium with 40% v/v of alcohol.

| Time in Hr. | % Drug Release | |
|---|---|---|
| | without EtOH | with 40% (v/v) EtOH |
| 0.00 | 0.00 | 0.00 |
| 0.25 | 0.00 | 0.00 |
| 0.50 | 0.00 | 0.05 |
| 0.75 | 0.10 | 0.50 |
| 1.00 | 0.20 | 0.83 |
| 1.50 | 0.40 | 5.68 |
| 2.00 | 0.50 | 11.61 |

(2) The formulation in Example 9 was analysed in 0.01 N HCl, USP (pH=2.0) for 2 hours and its corresponding alcoholic medium with 40% v/v of alcohol.

| Time in Hr. | % Drug Release | |
|---|---|---|
| | without EtOH | with 40% (v/v) EtOH |
| 0.00 | 0.00 | 0.00 |
| 0.25 | 0.00 | 0.00 |
| 0.50 | 0.01 | 0.12 |
| 0.75 | 0.25 | 0.80 |
| 1.00 | 0.30 | 1.02 |
| 1.50 | 0.45 | 8.95 |
| 2.00 | 0.60 | 12.61 |

(3) The formulation in Example 9 was analysed in pH 4.5, USP dissolution medium for 2 hours and its corresponding alcoholic medium with 40% v/v of alcohol.

| Time in Hr. | % Drug Release | |
|---|---|---|
| | without EtOH | With 40% (v/v) EtOH |
| 0.00 | 0.00 | 0.00 |
| 0.25 | 0.00 | 0.00 |
| 0.50 | 0.00 | 0.00 |
| 0.75 | 0.00 | 0.00 |
| 1.00 | 0.01 | 0.05 |
| 1.50 | 0.02 | 0.08 |
| 2.00 | 0.03 | 1.00 |

(4) The formulation in Example 9 was analysed in pH 6.8, USP dissolution medium for 12 hours and its corresponding alcoholic medium with 40% v/v of alcohol.

| Time in Hr. | % Drug Release | |
|---|---|---|
| | without EtOH | with 40% (v/v) EtOH |
| 0.00 | 0.00 | 0.00 |
| 1.00 | 0.10 | 6.2 |
| 2.00 | 20.32 | 34.62 |
| 3.00 | 47.89 | 54.21 |
| 4.00 | 70.32 | 89.32 |
| 5.00 | 79.35 | 94.56 |
| 6.00 | 85.78 | 99.56 |
| 7.00 | 96.45 | 100.00 |
| 8.00 | 100.00 | |

(5) The formulation in Example 9 was analysed in pH 7.4, USP dissolution medium for 12 hours and its corresponding alcoholic medium with 40% v/v of alcohol.

| Time in Hr. | % Drug Release | |
|---|---|---|
| | without EtOH | with 40% (v/v) EtOH |
| 0.00 | 0.00 | 0.00 |
| 1.00 | 2.20 | 0.98 |
| 2.00 | 35.23 | 26.56 |
| 3.00 | 65.32 | 55.24 |
| 4.00 | 88.89 | 75.32 |
| 5.00 | 95.23 | 84.45 |
| 6.00 | 99.23 | 89.14 |
| 7.00 | 100.00 | 92.87 |
| 8.00 | | 96.32 |
| 9.00 | | 100.00 |

Inference:

The release profiles prove the coated pellets prove to be pH dependent. Values of the release profiles of the coated pellets tested in 40% v/v hydro-alcoholic dissolution medium were resistant when compared with the release profiles of the coated pellets tested in dissolution medium without alcohol for all the time points.

Example 10

EUDRAGIT® NE 30 D/EUDRAGIT® L 30 D-55 (7:3)/Talc (125% w/w of the Polymer)/79% w/w Weight Gain by Coating Layer Formulation Details of Coating Suspension for 300 g of Cores

| Function | Ingredients | Quantity in g | Solids in g |
|---|---|---|---|
| Insoluble polymer | EUDRAGIT ® NE 30D | 247 | 74 |
| Soluble polymer | EUDRAGIT ® L 30D-55 | 103 | 31 |
| Lubricant | Talc | 131 | 131 |
| Diluent | Water, purified | 1092 | — |

Procedure:

Morphine sulphate pellets were coated with combination of EUDRAGIT® NE and EUDRAGIT® L 30 D-55 using 125% w/w of talc as an inert non-porous lubricant in coating suspension. The ratio of EUDRAGIT® NE 30 D dry substance and EUDRAGIT® L 30 D-55 dry substance (=EUDRAGIT® L 100-55) was 70%:30%. The coating was carried out in fluid bed processor using normal process parameters.

Dissolution Results:

Comparative release profiles in phosphate buffered saline pH 6.8, EP and corresponding alcoholic medium with 40% v/v alcohol.

| | % Drug Release | |
|---|---|---|
| Time in Hr. | without EtOH | with 40% (v/v) EtOH |
| 0.00 | 0 | 0 |
| 1.00 | 2.23 | 5.32 |
| 2.00 | 12.35 | 26.95 |
| 3.00 | 28.54 | 54.32 |
| 4.00 | 40.23 | 69.45 |
| 5.00 | 50.36 | 80.12 |
| 6.00 | 61.32 | 90.45 |
| 7.00 | 73.56 | 96.35 |
| 8.00 | 81.57 | 100.00 |
| 9.00 | 89.47 | |
| 10.00 | 95.98 | |
| 11.00 | 100.00 | |

Inference:

Values of the release profiles of the coated pellets tested in 40% v/v hydro-alcoholic dissolution medium were resistant when compared with the release profiles of the coated pellets tested in dissolution medium with out alcohol for all the time points.

Example 11

Inventive

EUDRAGIT® NE 30 D/EUDRAGIT® FS 30 D (7:3)/Talc (200% w/w of the Polymer)/165% w/w Weight Gain by Coating Layer Formulation Details of 55% w/w Coating Suspension for 300 g of Cores

| Function | Ingredients | Quantity in g | Solids in g |
|---|---|---|---|
| Insoluble polymer | EUDRAGIT ® NE 30D | 385 | 115.5 |
| Soluble polymer | EUDRAGIT ® FS 30D | 165 | 49.5 |
| Lubricant | Talc | 330 | 330.0 |
| Diluent | Water, purified | 2420 | — |

Procedure:

Morphine sulphate pellets were coated with a mixture of EUDRAGIT® NE 30D and EUDRAGIT® FS 30D at a ratio of 7:3 using 200% w/w talc as a lubricant in coating suspension. The coating was carried out in fluid bed processor using normal process parameters.

Dissolution Results:

Comparative release profiles in phosphate buffered saline pH 6.8, EP and corresponding alcoholic medium with 30% v/v alcohol.

| | % Drug Release | |
|---|---|---|
| Time in Hr. | without EtOH | with 30% (v/v) EtOH |
| 0.00 | 0.00 | 0.00 |
| 1.00 | 0.56 | 0.00 |
| 2.00 | 1.25 | 3.45 |
| 3.00 | 2.23 | 4.12 |
| 4.00 | 15.39 | 20.45 |
| 5.00 | 24.21 | 32.25 |
| 6.00 | 31.45 | 42.36 |
| 7.00 | 41.23 | 52.47 |
| 8.00 | 53.56 | 67.89 |
| 9.00 | 64.50 | 78.98 |
| 10.00 | 78.90 | 89.12 |
| 11.00 | 86.45 | 95.54 |
| 12.00 | 94.78 | 99.21 |
| 14.00 | 98.97 | |
| 16.00 | 100.00 | |

Inference:

Values of the release profiles of the coated pellets tested in 30% v/v hydro-alcoholic dissolution medium were resistant when compared with the release profiles of the coated pellets tested in dissolution medium with out alcohol for all the time points.

Dissolution Results:

Comparative release profiles in phosphate buffered saline pH 6.8, EP and corresponding alcoholic medium with 40% v/v alcohol.

| | % Drug Release | |
|---|---|---|
| Time in Hr. | Without EtOH | with 40% (v/v) EtOH |
| 0.00 | 0.00 | 0.00 |
| 1.00 | 0.56 | 1.25 |
| 2.00 | 1.25 | 5.45 |
| 3.00 | 2.23 | 8.54 |
| 4.00 | 15.39 | 23.54 |
| 5.00 | 24.21 | 38.45 |
| 6.00 | 31.45 | 47.64 |
| 7.00 | 41.23 | 58.78 |
| 8.00 | 53.56 | 73.45 |
| 9.00 | 64.50 | 85.95 |
| 10.00 | 78.90 | 96.23 |
| 11.00 | 86.45 | 99.45 |
| 12.00 | 94.78 | |
| 13.00 | 98.97 | |
| 14.00 | 100.00 | |

Inference:

Values of the release profiles of the coated pellets tested in 40% v/v hydro-alcoholic dissolution medium were resistant when compared with the release profiles of the coated pellets tested in dissolution medium with out alcohol for all the time points.

Example 12

Comparative Example

EUDRAGIT® NE 30D/EUDRAGIT® FS 30D, 7:3/Lubricant: Glyceryl Monostearate (GMS) (50% w/w of the Polymer)/84% w/w Coating/Core Formulation Details of Coating Suspension for 300 g of Cores

| Function | Ingredients | Quantity in g | Solids in g |
|---|---|---|---|
| Insoluble polymer | EUDRAGIT ® NE 30D | 385 | 115.5 |
| Soluble polymer | EUDRAGIT ® FS 30D | 165 | 49.5 |

| Function | Ingredients | Quantity in g | Solids in g |
|---|---|---|---|
| Lubricant | GMS | 83 | 83 |
| Emulsifier | Tween 80 | 3.3 | 3.3 |
| Diluent | Water, purified | 1205 | — |

Procedure:

Morphine sulphate pellets were supposed to be coated with a mixture of EUDRAGIT® NE 30D and EUDRAGIT® FS 30D at a ratio 7:3 using 50% w/w of Glyceryl monostearate as a lubricant in coating suspension. The coating was intended to be applied in fluid bed processor using normal process parameters.

Note:

Coating of drug loaded pellets using combination of EUDRAGIT® NE 30D and EUDRAGIT® FS 30D with 50% w/w GMS as a lubricant in a coating suspension was not practically feasible because of nozzle blocking.

The invention claimed is:

1. A pH-dependent controlled release pharmaceutical composition, comprising
a core, comprising at least one pharmaceutical active ingredient, which is an opioid, wherein the core is coated by at least one coating layer, controlling the release of the pharmaceutical composition,
wherein the coating layer comprises a polymer mixture of
i) 40-95% by weight, based on dry weight of the polymer mixture, of at least one water insoluble essentially neutral vinyl polymer or copolymer, and
ii) 5-60% by weight, based on dry weight of the polymer mixture, of at least one anionic polymer or copolymer, which is insoluble in a buffered medium below pH 4.0 and soluble at least in the range from pH 7.0 to pH 8.0,
wherein
the coating layer further comprises 110 to 250% by weight, calculated on dry weight of the polymer mixture, of a non-porous inert lubricant and the coating layer is present in an amount of at least 60% by weight calculated on the weight of core, and
wherein, under in-vitro conditions according to USP paddle, 100 rpm, buffered at pH 6.8 in a medium with and without the addition of 40% (v/v) ethanol:
when the pharmaceutical active ingredient is released to a degree of less than 20% without the addition of 40% (v/v) ethanol, the difference in the release rate with the addition of 40% (v/v) ethanol is not more than plus or minus 15% of the corresponding release value without 40% (v/v) ethanol, and
when the pharmaceutical active ingredient is released to a degree of 20-80% without the addition of 40% (v/v) ethanol, the difference in the release rate with the addition of 40% (v/v) ethanol is not more than plus or minus 30% of the corresponding release value without 40% (v/v) ethanol.

2. The controlled release pharmaceutical composition according to claim 1 wherein the non-porous inert lubricant is a layered silica component, a pigment or a stearate compound.

3. The controlled release pharmaceutical composition according to claim 2 wherein the inert lubricant is talc.

4. The controlled release pharmaceutical composition according to claim 2 wherein the inert lubricant is Ca- or Mg-stearate.

5. The controlled release pharmaceutical composition according to claim 1, wherein the water insoluble essentially neutral vinyl polymer or copolymer is a copolymer composed of free-radical polymerized units of more than 95 up to 100% by weight $C_1$- to $C_4$-alkyl esters of acrylic or of methacrylic acid and less than 5% by weight of acrylic or methacrylic acid.

6. The controlled release pharmaceutical composition according to claim 1, wherein the water insoluble essentially neutral polymer is a polyvinyl acetate type polymer or copolymer.

7. The controlled release pharmaceutical composition according to claim 1, wherein the anionic polymer is a (meth)acrylate copolymer composed of free-radical polymerized units of 25 to 95% by weight $C_1$- to $C_4$-alkyl esters of acrylic or of methacrylic acid and 5 to 75% by weight (meth)acrylate monomers having an anionic group.

8. The controlled release pharmaceutical composition according to claim 1, wherein the opioid comprises a member selected from the group consisting of morphine, codeine and thebaine, diamorphine (heroin), oxycodone, hydrocodone, dihydrocodeine, hydromorphone, oxymorphone, nicomorphine, methadone, levomethadyl acetate hydrochloride (LAAM), pethidine (meperidine), ketobemidone, propoxyphene, dextropropoxyphene, dextromoramide, bezitramide, piritramide, pentazocine or phenazocine, hydromorphine, hydrocodone, oxymorphone, oxycodone, buprenorphine, hydromorphone, levorphanol, tramadol, tilidine, sufentanil, pentozocine, nalbuphine, meptazinol, meperidine and fentanyl including pharmaceutically acceptable salts, free base or free acid forms or mixtures of said substances.

9. The controlled release pharmaceutical composition according to claim 1 wherein it is in the form of pellets contained in a multiparticulate pharmaceutical form of compressed tablets, capsules, sachets, effervescent tablets or reconstitutable powders.

10. The controlled release pharmaceutical composition according to claim 1 equipped with a sub coat or a top coat, or both.

11. The controlled release pharmaceutical composition according to claim 1 present in the form of coated pellets or minitablets with an overall average diameter in the range of from 100 to 3000 μm.

12. The controlled release pharmaceutical composition according to claim 1 wherein the resulting coated pellets have an overall average diameter in the range of between 100 to 700 μm.

13. The controlled release pharmaceutical composition according to claim 1 wherein the resulting coated pellets or minitablets have an overall average diameter in the range of between 1400 to 3000 μm.

14. A method of reducing the risk of enhanced or reduced release of an included pharmaceutical active ingredient after oral ingestion by simultaneous or subsequent consumption of ethanol containing drinks comprising employing a pH-dependent controlled release pharmaceutical composition according to claim 1.

15. A method of reducing the risk of abuse of an included pharmaceutical active ingredient by in-vitro extraction using ethanol containing media before oral ingestion comprising employing a pH-dependent controlled release pharmaceutical composition according to claim 1.

16. The controlled release pharmaceutical composition according to claim 1, wherein the water insoluble essentially neutral vinyl polymer or copolymer is composed of 20 to 40% by weight of ethyl acrylate, 60 to 80% by weight of methyl methacrylate and 0 to less than 5% by weight of acrylic acid or methacrylic acid, and the anionic polymer or copolymer consists of 10 to 30% by weight methyl methacrylate, 50 to 70% by weight methyl acrylate and 5 to 15% by weight methacrylic acid.

\* \* \* \* \*